United States Patent
Kulbis

(10) Patent No.: US 10,500,143 B2
(45) Date of Patent: Dec. 10, 2019

(54) REFLECTIVE SKIN-SPREAD COMPOSITION

(71) Applicant: ROAD WISE LLC, Cleveland Heights, OH (US)

(72) Inventor: John F. Kulbis, Cleveland Heights, OH (US)

(73) Assignee: ROAD WISE LLC, Cleveland Heights, OH (US)

( * ) Notice: Subject to any disclaimer, the term of this patent is extended or adjusted under 35 U.S.C. 154(b) by 0 days.

(21) Appl. No.: 16/342,467

(22) PCT Filed: Nov. 29, 2017

(86) PCT No.: PCT/US2017/063604
§ 371 (c)(1),
(2) Date: Apr. 16, 2019

(87) PCT Pub. No.: WO2018/102349
PCT Pub. Date: Jun. 7, 2018

(65) Prior Publication Data
US 2019/0336418 A1    Nov. 7, 2019

Related U.S. Application Data

(60) Provisional application No. 62/427,214, filed on Nov. 29, 2016.

(51) Int. Cl.
| | | |
|---|---|---|
| *A61K 8/25* | (2006.01) | |
| *A61K 8/26* | (2006.01) | |
| *A61K 8/92* | (2006.01) | |
| *A61K 8/362* | (2006.01) | |
| *A61Q 1/02* | (2006.01) | |
| *A61K 8/81* | (2006.01) | |

(52) U.S. Cl.
CPC .............. *A61K 8/25* (2013.01); *A61K 8/26* (2013.01); *A61K 8/362* (2013.01); *A61K 8/8182* (2013.01); *A61K 8/92* (2013.01); *A61Q 1/02* (2013.01)

(58) Field of Classification Search
CPC ... A61K 8/25; A61K 8/26; A61K 8/92; A61K 8/362; A61K 8/8182; A61Q 1/02
See application file for complete search history.

(56) References Cited

U.S. PATENT DOCUMENTS

| | | |
|---|---|---|
| 5,000,937 A | 3/1991 | Grollier et al. |
| 6,403,068 B1 | 6/2002 | Stein |
| 2010/0031969 A1 | 2/2010 | Lezer et al. |
| 2010/0150853 A1 | 6/2010 | Cassin et al. |
| 2015/0272840 A1 | 10/2015 | Liu et al. |
| 2016/0101033 A1 | 4/2016 | Finjan et al. |

FOREIGN PATENT DOCUMENTS

WO    2013107776 A2    7/2013

OTHER PUBLICATIONS

Prizmalite Industries Inc., "Prizmalite, Material Safety Data Sheet, P2453BTA Metallized Glass Microspheres," 2012, 2 pages.
Prizmalite Industries Inc., "Prizmalite, Specifications, Prizmalite P2453BTA, Metallized Glass Microspheres," 2012, 1 page.
Bluestar Silicones USA Corp., "Silbione RTV 4410 QC A/B, Elastomer for Special Effects Applications," 2012, 2 pages.
Bluestar Silicones USA Corp., "Silbione RTV 4410 QCC A, Safety Data Sheet," 2015, 10 pages.
Bluestar Silicones USA Corp., "Silbione RTV 4410 QCC B, Safety Data Sheet," 2015, 10 pages.
Silicone Solutions, "SS-232B Silicone Product, Material Safety Data Sheet," 2013, 3 pages.
International Search Report and Written Opinion issued in application No. PCT/US2017/63604 dated Feb. 14, 2018, 16 pages.

*Primary Examiner* — Zohreh A Fay
(74) *Attorney, Agent, or Firm* — Pearne & Gordon LLP

(57) ABSTRACT

A reflective skin-spread composition is provided. The composition comprises 80 to 90 w/w % reflective glass microspheres, and 10 to 20 w/w % carrier medium. The reflective glass microspheres have an average diameter of 30 to 80 microns. The carrier medium comprises an emollient ester, a plant emollient, a binder/stabilizer, and a water-resistant film-forming agent. The composition comprises the emollient ester at 3 to 6 w/w %, the plant emollient at 2 to 5 w/w %, the binder/stabilizer at 3 to 6 w/w %, and the water-resistant film-forming agent at 1 to 4 w/w %. An applicator for applying the composition to a surface also is provided. A method of enhancing visibility of a person comprising a step of applying the composition to an exposed skin surface of the person also is provided.

20 Claims, 3 Drawing Sheets

REFLECTIVE SKIN-SPREAD COMPOSITION

CROSS-REFERENCES TO RELATED APPLICATIONS

This application claims the benefit of U.S. Provisional Application No. 62/427,214, filed Nov. 29, 2016, which is incorporated herein by reference.

FIELD OF THE INVENTION

The invention relates to a reflective skin-spread composition, and more particularly to a reflective skin-spread composition comprising (a) 80 to 90 weight/weight percent (also termed w/w %) reflective glass microspheres; and (b) 10 to 20 w/w % carrier medium; wherein: (i) the reflective glass microspheres have an average diameter of 30 to 80 microns; (ii) the carrier medium comprises an emollient ester, a plant emollient, a binder/stabilizer, and a water-resistant film-forming agent; and (iii) the composition comprises the emollient ester at 3 to 6 w/w %, the plant emollient at 2 to 5 w/w %, the binder/stabilizer at 3 to 6 w/w %, and the water-resistant film-forming agent at 1 to 4 w/w %.

BACKGROUND OF THE INVENTION

Many people, including runners, walkers, cyclists, and others, use roads, sidewalks, trails, and paths for exercise, play, and/or commuting during periods of relatively poor visibility, particularly dusk, night, and dawn. The poor visibility creates a risk for such people that they may not be seen by motorists, other cyclists, and others who are also using the roads, sidewalks, trails, and paths and who may be moving quickly, such that the people may be struck accidentally, resulting in their injury and/or death. Runners, walkers, cyclists, and others can make themselves easier to see by wearing clothing that is brightly colored, illuminated, and/or reflective. Such clothing can be expensive and/or cumbersome to wear though. As an alternative, Stein's U.S. Pat. No. 6,403,068 discloses a brightly colored composition, including a brightly colored or fluorescent compound, that may be quickly applied to a person's skin to increase visibility while exercising or travelling by foot, bicycle, or the like. According to Stein, the composition includes a base carrier medium such as a lotion, cream, gel, or the like having a coloring agent dissolved or otherwise disposed therein, generally at about 1 to 60 w/w %, and also includes an antiperspirant to minimize degradation due to excessive sweating while exercising. Improving visibility based on use of a brightly colored or fluorescent compound may be inefficient, though. Moreover, use of an antiperspirant to minimize degradation of a composition intended to increase visibility may be undesirable, e.g. due to irritation. Accordingly, a need exists for improved compositions and methods for increasing visibility of people, such as runners, walkers, cyclists, and others, using roads, sidewalks, trails, and paths.

BRIEF SUMMARY OF THE INVENTION

A reflective skin-spread composition is provided. The composition comprises: (a) 80 to 90 w/w % reflective glass microspheres; and (b) 10 to 20 w/w % carrier medium. The reflective glass microspheres have an average diameter of 30 to 80 microns. The carrier medium comprises an emollient ester, a plant emollient, a binder/stabilizer, and a water-resistant film-forming agent. The composition comprises the emollient ester at 3 to 6 w/w %, the plant emollient at 2 to 5 w/w %, the binder/stabilizer at 3 to 6 w/w %, and the water-resistant film-forming agent at 1 to 4 w/w %.

An applicator for applying the composition to a surface also is provided. The applicator comprises (i) an elongate container comprising (a) a side wall having a top end and an opposite bottom end, (b) a base at the bottom end of the side wall, and (c) the composition. The top end of the side wall defines an opening of the container. The side wall and the base define a reservoir in the container. The composition is disposed in the reservoir. The applicator also comprises (ii) a cap removably attached to the container at the side wall and covering the opening. The composition is in a solid form. The reflective glass microspheres are substantially homogeneously distributed within the composition. The composition is slidably engaged in the reservoir such that the composition can be pushed outwardly from the reservoir through the opening.

A method of enhancing visibility of a person also is provided. The method comprises a step of applying the composition to an exposed skin surface of the person.

The reflective skin-spread composition can comprise, for example, (a) 80 to 90 w/w % aluminum metal coated barium titanate glass microspheres; (b) 3 to 6 w/w % C12-C15 alkyl benzoate; (c) 2 to 5 w/w % caprylic/capric triglyceride; (d) 3 to 6 w/w % mineral wax; (e) 1 to 4 w/w % a synthetic polymer of a hydrocarbon eicosene and vinylpyrrolidone; (f) 0.5 to 1.2 w/w % carnauba wax; and (g) 0.1 to 0.3 w/w % tocopherol acetate.

BRIEF DESCRIPTION OF THE DRAWINGS

Referring now to the drawings in which like reference numbers represent corresponding parts throughout.

DETAILED DESCRIPTION OF THE INVENTION

Figure 1:
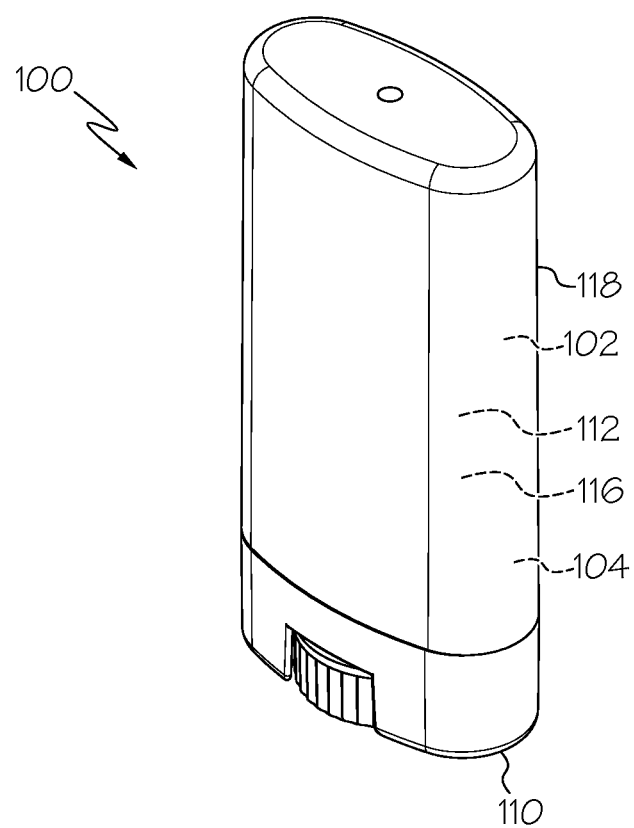
FIG. 1 shows an exemplary applicator for applying the composition, in perspective view.

A reflective skin-spread composition is provided. The composition comprises: (a) 80 to 90 w/w % reflective glass microspheres; and (b) 10 to 20 w/w % carrier medium. The reflective glass microspheres have an average diameter of 30 to 80 microns. The carrier medium comprises an emollient ester, a plant emollient, a binder/stabilizer, and a water-resistant film-forming agent. The composition comprises the emollient ester at 3 to 6 w/w %, the plant emollient at 2 to 5 w/w %, the binder/stabilizer at 3 to 6 w/w %, and the water-resistant film-forming agent at 1 to 4 w/w %.

Without wishing to be bound by theory, it is believed that by formulating the composition to comprise (a) 80 to 90 w/w % reflective glass microspheres, and (b) 10 to 20 w/w % carrier medium, such that the reflective glass microspheres have an average diameter of 30 to 80 microns, the carrier medium comprises an emollient ester, a plant emollient, a binder/stabilizer, and a water-resistant film-forming agent, and the composition comprises the emollient ester at 3 to 6 w/w %, the plant emollient at 2 to 5 w/w %, the binder/stabilizer at 3 to 6 w/w %, and the water-resistant film-forming agent at 1 to 4 w/w %, that surprisingly the composition can be prepared such that the reflective glass microspheres are substantially homogeneously distributed within the composition during preparation of the composition, dispensing of the composition into an applicator, solidification of the composition in the applicator, and formation of a film on an exposed skin surface of a person. The formulation allows the composition to flow sufficiently when maintained at a preparation temperature that is greater than ambient temperature to allow the reflective glass microspheres to be mixed uniformly within the composition during preparation, such that the reflective glass microspheres can be homogenously distributed within the composition, despite the reflective glass microspheres being present at 80 to 90 w/w % in the composition. The formulation also allows the composition to flow sufficiently when maintained at a dispensing temperature that also is greater than ambient temperature to allow the composition to be dispensed into the applicator without having the reflective glass microspheres settle substantially in the composition, such that the reflective glass microspheres can remain homogenously distributed within the composition. The formulation also allows the composition to solidify rapidly when cooled from a dispensing temperature to ambient temperature, also without having the reflective glass microspheres settle substantially in the composition, such that the reflective glass microspheres can remain homogenously distributed within the composition. The formulation also allows the composition to form a film that is highly reflective when applied to an exposed skin surface of a person, with the film being permeable to perspiration and resistant to degradation from perspiration, and remaining highly reflective even as the exposed skin surface rises in temperature, e.g. during exertion associated with exercise. Upon application of the composition to the exposed skin surface of the person, the resulting film is particularly effective at reflecting beams of light from headlights of motor vehicles such as cars and trucks, so as to improve visibility of the person to motorists operating such motor vehicles.

In some examples, the carrier medium is anhydrous. In accordance with these examples, the carrier medium can be free of water.

In some examples, the composition does not comprise latex. In accordance with these examples, the composition can form a film on an exposed skin surface of a person, without need for use of latex to form the film, and thus without risking an allergic response in the person due to latex.

In some examples, the composition does not comprise silicone. In accordance with these examples, the composition can form a film on an exposed skin surface of a person, without need for use of silicone to form the film, and thus without need for use of a two part silicone-based curing process, which was observed to be inconsistent with maintaining a homogeneous distribution of reflective glass microspheres during application and curing.

In some examples, the composition does not comprise an antiperspirant agent. The composition can form a film on an exposed skin surface of a person such that the film is permeable to perspiration and resistant to degradation from perspiration, thus obviating any potential need to include an antiperspirant agent in the composition in order to maintain the integrity of the film formed from the composition, e.g. during exercise, play, and/or commuting. Antiperspirant agents that thus can be omitted from the composition include, for example, aluminium chloride, aluminium chlorohydrate, and aluminium-zirconium compounds, among others. Thus, in accordance with these examples, the composition does not comprise any aluminium chloride, aluminium chlorohydrate, and aluminium-zirconium compounds, among other antiperspirant agents.

In some examples, the reflective glass microspheres comprise aluminum metal coated barium titanate glass microspheres. Suitable examples include PRIZMALITE P2453BTA metallized glass microspheres, which are hemispherically aluminum coated barium titanate glass microspheres with an average diameter of 40 to 50 microns, and which are commercially available from PRIZMALITE INDUSTRIES (New York, N.Y.).

In some examples, the emollient ester comprises C12-C15 alkyl benzoate.

In some examples, the plant emollient comprises caprylic/capric triglyceride.

In some examples, the binder/stabilizer comprises mineral wax.

In some examples, the water-resistant film-forming agent comprises a synthetic polymer of a hydrocarbon eicosene and vinylpyrrolidone.

In some examples, the composition further comprises a thickener/emollient and an antioxidant. In accordance with these examples, the thickener/emollient can be, for example, carnauba wax. Also in accordance with these examples, the antioxidant can be, for example, tocopherol acetate.

Figure 2:
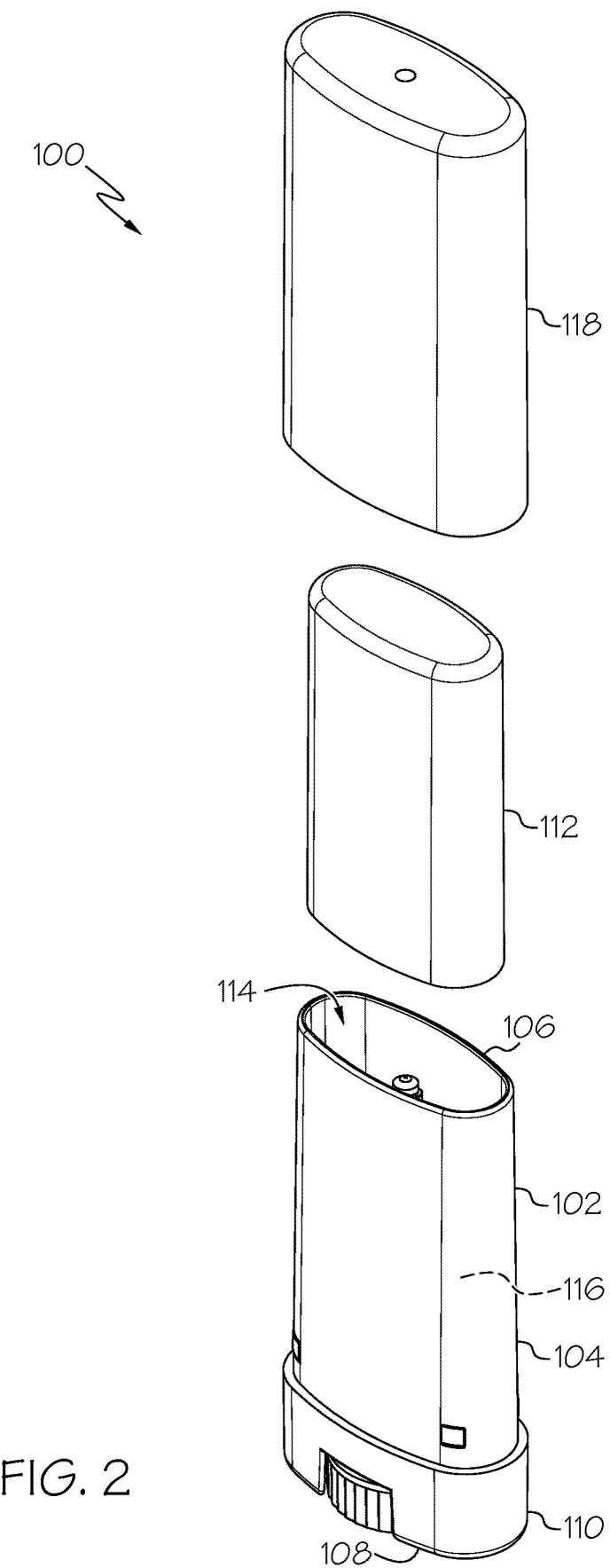
FIG. 2 shows the applicator of FIG. 1 in exploded view, in perspective view.

An applicator for applying the composition to a surface also is provided. As shown in FIG. 1 and FIG. 2, the applicator 100 comprises (i) an elongate container 102 comprising (a) a side wall 104 having a top end 106 and an opposite bottom end 108, (b) a base 110 at the bottom end 108 of the side wall 104, and (c) the composition 112. The top end 106 of the side wall 104 defines an opening 114 of the container 102. The side wall 104 and the base 110 define a reservoir 116 in the container 102. The composition 112 is disposed in the reservoir 116. The applicator 100 also comprises (ii) a cap 118 removably attached to the container 102 at the side wall 104 and covering the opening 114. The composition 112 is in a solid form. The reflective glass microspheres are substantially homogeneously distributed within the composition 112. The composition 112 is slidably engaged in the reservoir 116 such that the composition 112 can be pushed outwardly from the reservoir 116 through the opening 114. The applicator can have a structure typical of applicators in the field of cosmetics, e.g. spread-on-type applicators of sunscreen compositions, including for example propel/repel-type containers, among others.

As noted, the reflective glass microspheres are substantially homogeneously distributed within the composition 112. By substantially homogenously distributed, it is meant that the concentration of the reflective glass microspheres varies less than 10% across the composition 112. For example, the concentration of the reflective glass microspheres can vary less than 9%, less than 8%, less than 7%, less than 6%, less than 5%, less than 4%, less than 3%, less than 2%, or less than 1% across the composition 112.

In accordance with some examples, the container 102 has a length between the base 110 and the opening 114, as measured within the reservoir 116, of at least 4 cm and the reservoir 116 has a volume of at least 12 ml. In accordance with these examples, and as discussed above, surprisingly the composition 112 can be prepared such that the reflective glass microspheres are substantially homogeneously distributed within the composition 112 during preparation of the composition 112, dispensing of the composition 112 into an applicator 100, solidification of the composition 112 in the applicator 100, and formation of a film on an exposed skin surface of a person. This is so despite the container 102 having a length between the base 110 and the opening 114, as measured within the reservoir 116, of at least 4 cm and the reservoir 116 having a volume of at least 12 ml, which may have been expected to result in substantial settling of the reflective glass microspheres in the composition 112 during dispensing of the composition 112 in the applicator 100 before solidification of the composition 112 in the applicator 100.

A method of enhancing visibility of a person also is provided. The method comprises a step of applying the composition to an exposed skin surface of the person. The person can be, for example, a runner, a walker, or a cyclist, among others.

In some examples, the step of applying the composition comprises swiping the composition back and forth on the exposed skin surface.

In some examples, the method further comprises, after the step of applying the composition, a step of removing a film formed from the composition from the exposed skin surface by contacting the film with a wet wipe and/or soap and water. Although the formulation allows the composition to form a film that is highly reflective when applied to an exposed skin surface of a person, with the film being permeable to perspiration and resistant to degradation by perspiration, and remaining highly reflective even as the exposed skin surface rises in temperature, e.g. during exertion associated with exercise, the formulation also allows the film to be removed from the skin conveniently following use, by contacting the film with a wet wipe, e.g. by wiping the wet wipe back and forth across the film several times, and/or by contacting the film with soap and water, e.g. by gently scrubbing the film.

In some examples, the exposed skin surface of the person is at least one of an exposed skin surface of the face, the chest, the back, one or both arms, or one or both legs of the person. Because the formulation allows the composition to form a film that is highly reflective when applied to an exposed skin surface of a person, with the film being permeable to perspiration and resistant to degradation from perspiration, and remaining highly reflective even as the exposed skin surface rises in temperature, e.g. during exertion associated with exercise, the composition can be applied advantageously to exposed skin surfaces, such as those of the face, the chest, the back, one or both arms, or one or both legs, that would tend to be visible to others, including for example motorists, other cyclists, etc., and this is so even to the extent that such exposed skin surfaces may also tend to perspire excessively, e.g. during exertion associated with exercise.

In some examples, the composition is applied from an applicator as described above. In accordance with these examples, the applicator 100 comprises (i) an elongate container 102 comprising (a) a side wall 104 having a top end 106 and an opposite bottom end 108, (b) a base 110 at the bottom end 108 of the side wall 104, and (c) the composition 112. The top end 106 of the side wall 104 defines an opening 114 of the container 102. The side wall 104 and the base 110 define a reservoir 116 in the container 102. The composition 112 is disposed in the reservoir 116. The applicator 100 also comprises (ii) a cap 118 removably attached to the container 102 at the side wall 104 and covering the opening 114. The composition 112 is in a solid form. The reflective glass microspheres are substantially homogeneously distributed within the composition 112. The composition 112 is slidably engaged in the reservoir 116 such that the composition 112 can be pushed outwardly from the reservoir 116 through the opening 114.

In accordance with these examples, the method further comprises, prior to the step of applying the composition 112, a step of removing the cap 118 from the container 102 at the side wall 104. This exposes the composition 112 in the container 102 such that the composition 112 can be applied to the exposed skin surface.

In some embodiments of these examples, the method further comprises, between the steps of removing the cap 118 and applying the composition 112, a step of pushing the composition 112 outwardly from the reservoir 116 through the opening 114. This ensures that composition 112 can make contact with the exposed skin surface.

The reflective skin-spread composition can comprise, for example, (a) 80 to 90 w/w % aluminum metal coated barium titanate glass microspheres; (b) 3 to 6 w/w % C12-C15 alkyl benzoate; (c) 2 to 5 w/w % caprylic/capric triglyceride; (d) 3 to 6 w/w % mineral wax; (e) 1 to 4 w/w % a synthetic polymer of a hydrocarbon eicosene and vinylpyrrolidone; (f) 0.5 to 1.2 w/w % carnauba wax; and (g) 0.1 to 0.3 w/w % tocopherol acetate.

EXAMPLES

My idea for the reflective skin-spread composition was based on my inadvertently leaning against a surface coated with wet white paint while I was painting the interior of a home. Cleaning up that day, the white stripe of paint, which transferred from the wall to the back of my arm, was relentless in its removal. Later, during my evening run, as cars and trucks passed me, I noticed that the stripe of paint reflected light from the headlights of the cars and trucks. This inspired me to try to develop a reflective skin-spread composition that could be applied to exposed skin surfaces to form a film that would be sufficiently reflective so as to increase visibility, that would be permeable to perspiration, that would remain intact despite perspiration, and that could nonetheless be removed easily by contact with a wet wipe and/or soap and water.

After much trial and error, including developing compositions including latex or medical-grade silicones that seemed promising but that ultimately turned out to be unsuitable, I realized that the reflective particles were the most important ingredient, and I began research and development using waxes for the base. Due to the range of melting temperatures that various waxes have, I determined that selecting a suitable wax and other base ingredients would help the composition apply smoothly on the skin. I determined that a wax with too low of a melting temperature would not last the duration of exercise, as heat sheds the body, and would not hold up during warm weather activities. Conversely, a wax with too high of a melting temperature would remain too firm during application, thus not transferring to the skin. Moreover, if the composition was too greasy, an effect caused by the other ingredients in the base medium, that greasiness would also block the reflectivity of the reflective particles, prohibiting light from reflecting back to its source.

A key component of successfully getting this wax-based medium to work was mixing and pouring the waxes at a specific temperature. If the formulation was poured at too high of a temperature into an applicator, then upon cooling the reflective particles would settle within the composition, toward the base of the applicator. This would yield a composition having little or no reflective particles at the top of the composition, and most or all of the reflective particles located near the base of the composition, making the composition unsuitable. The correct pouring temperature yielded a composition that remained homogenously mixed within the applicator, containing the reflective particles substantially homogeneously distributed throughout the composition. This homogenous mixture promoted the balance of reflective particles to medium, so that the reflective particles were present in every swipe upon application of the composition to an exposed skin surface. Moreover, following passing over the same area of skin with multiple swipes, the reflective particles remained present at the top layer of the film on the exposed skin surface, and thus reflected the light back to the source as intended.

An exemplary formulation for the reflective skin-spread composition is provided in TABLE 1.

TABLE 1

Exemplary formulation for the reflective skin-spread composition.

| Ingredient | Weight/Weight % | INCI NAME | FUNCTION |
|---|---|---|---|
| FINSOLV (R) TN emollient ester | 4.0700 | C12-C15 Alkyl Benzoate | Emollient ester |
| Coconut oil fractionated | 3.5700 | Caprylic/capric triglyceride | Plant emollient |
| Ceresine wax | 4.1600 | Mineral wax | Binder/stabilizer |
| GANEX (TM) v-220 film former | 2.1500 | Vp/Eicosene copolymer | Water resistant film forming agent |
| Carnauba wax | 0.8300 | Copernicia prunifera wax | Thickener/emollient |
| Tocopherol Acetate | 0.2200 | Vitamin E Acetate | Antioxidant |
| PRIZMALITE P2453BTA metallized glass microspheres | 85.00 | Microsphere Barium Titanate | Reflective particles |
| Total | 100.00 | | |

Figure 3:
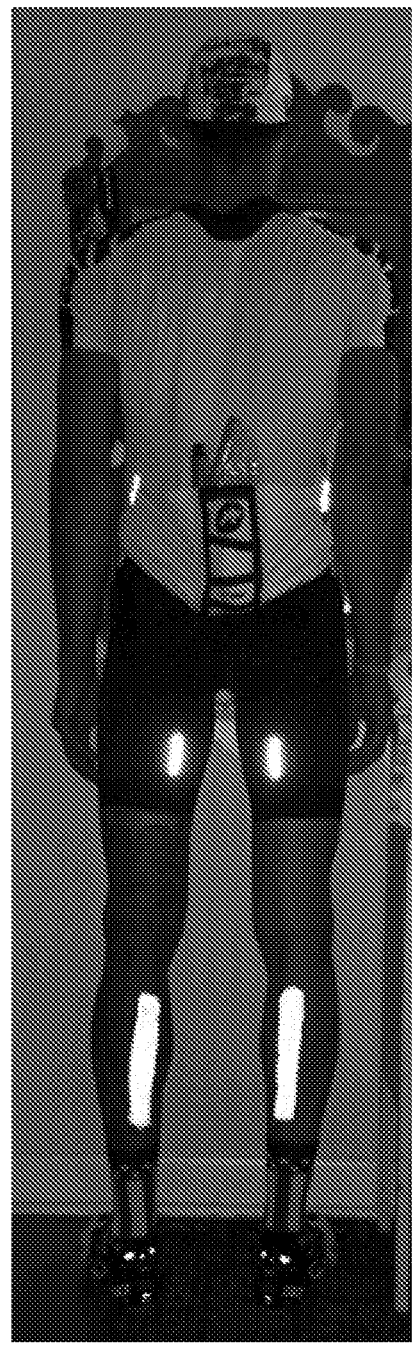
FIG. 3 is a photograph of an example of the reflective skin-spread composition, as applied to an exposed skin surface of a person, demonstrating reflectivity of a film formed from the composition.

A photograph of the reflective skin-spread composition, as applied to an exposed skin surface of a person, demonstrating reflectivity of a film formed from the composition, is shown in FIG. 3.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

The invention claimed is:

1. A reflective skin-spread composition comprising:
   (a) 80 to 90 w/w % reflective glass microspheres; and
   (b) 10 to 20 w/w % carrier medium;
   wherein:
   (i) the reflective glass microspheres have an average diameter of 30 to 80 microns;
   (ii) the carrier medium comprises an emollient ester, a plant emollient, a binder/stabilizer, and a water-resistant film-forming agent; and
   (iii) the composition comprises the emollient ester at 3 to 6 w/w %, the plant emollient at 2 to 5 w/w %, the binder/stabilizer at 3 to 6 w/w %, and the water-resistant film-forming agent at 1 to 4 w/w %.

2. The composition of claim 1, wherein the carrier medium is anhydrous.

3. The composition of claim 1, wherein the composition does not comprise latex.

4. The composition of claim 1, wherein the composition does not comprise silicone.

5. The composition of claim 1, wherein the composition does not comprise an antiperspirant agent.

6. The composition of claim 1, wherein the reflective glass microspheres comprise aluminum metal coated barium titanate glass microspheres.

7. The composition of claim 1, wherein the emollient ester comprises C12-C15 alkyl benzoate.

8. The composition of claim 1, wherein the plant emollient comprises caprylic/capric triglyceride.

9. The composition of claim 1, wherein the binder/stabilizer comprises mineral wax.

10. The composition of claim 1, wherein the water-resistant film-forming agent comprises a synthetic polymer of a hydrocarbon eicosene and vinylpyrrolidone.

11. The composition of claim 1, further comprising a thickener/emollient and an antioxidant.

12. An applicator for applying the composition of claim 1 to a surface, the applicator comprising:
   (i) an elongate container comprising (a) a side wall having a top end and an opposite bottom end, (b) a base at the bottom end of the side wall, and (c) the composition, wherein the top end of the side wall defines an opening of the container, the side wall and the base define a reservoir in the container, and the composition is disposed in the reservoir; and
   (ii) a cap removably attached to the container at the side wall and covering the opening,
   wherein:
   the composition is in a solid form;
   the reflective glass microspheres are substantially homogeneously distributed within the composition; and
   the composition is slidably engaged in the reservoir such that the composition can be pushed outwardly from the reservoir through the opening.

13. The applicator of claim 12, wherein the container has a length between the base and the opening, as measured within the reservoir, of at least 4 cm and the reservoir has a volume of at least 12 ml.

14. A method of enhancing visibility of a person comprising a step of:
   applying the composition of claim 1 to an exposed skin surface of the person.

15. The method of claim 14, wherein the step of applying the composition comprises swiping the composition back and forth on the exposed skin surface.

16. The method of claim 14, further comprising, after the step of applying the composition, a step of removing a film formed from the composition from the exposed skin surface by contacting the film with a wet wipe and/or soap and water.

17. The method of claim 14, wherein the exposed skin surface of the person is at least one of an exposed skin surface of the face, the chest, the back, one or both arms, or one or both legs of the person.

18. The method of claim 14, wherein the composition is applied from an applicator comprising:
   (i) an elongate container comprising (a) a side wall having a top end and an opposite bottom end, (b) a base at the bottom end of the side wall, and (c) the composition, wherein the top end of the side wall defines an opening of the container, the side wall and the base define a reservoir in the container, and the composition is disposed in the reservoir; and
   (ii) a cap removably attached to the container at the side wall and covering the opening,
   wherein:
   the composition is in a solid form;
   the reflective glass microspheres are substantially homogeneously distributed within the composition; and
   the composition is slidably engaged in the reservoir such that the composition can be pushed outwardly from the reservoir through the opening;
   the method further comprising, prior to the step of applying the composition, a step of removing the cap from the container at the side wall.

19. The method of claim 18, further comprising, between the steps of removing the cap and applying the composition, a step of pushing the composition outwardly from the reservoir through the opening.

20. A reflective skin-spread composition comprising:
   (a) 80 to 90 w/w % aluminum metal coated barium titanate glass microspheres;
   (b) 3 to 6 w/w % C12-C15 alkyl benzoate;
   (c) 2 to 5 w/w % caprylic/capric triglyceride;
   (d) 3 to 6 w/w % mineral wax;
   (e) 1 to 4 w/w % a synthetic polymer of a hydrocarbon eicosene and vinylpyrrolidone;
   (f) 0.5 to 1.2 w/w carnauba wax; and
   (g) 0.1 to 0.3 w/w % tocopherol acetate.

* * * * *